US009202457B2

(12) United States Patent
Song et al.

(10) Patent No.: US 9,202,457 B2
(45) Date of Patent: Dec. 1, 2015

(54) APPARATUS FOR DRIVING TWO-DIMENSIONAL TRANSDUCER ARRAY, MEDICAL IMAGING SYSTEM, AND METHOD OF DRIVING TWO-DIMENSIONAL TRANSDUCER ARRAY

(75) Inventors: Jong-keun Song, Yongin-si (KR); Oh-kyong Kwon, Seoul (KR); Kyung-il Cho, Seoul (KR); Dong-wook Kim, Seoul (KR); Bae-hyung Kim, Seoul (KR)

(73) Assignees: Samsung Electronics Co., Ltd., Suwon-si (KR); Industry-University Cooperation Foundation Hanyang University, Seoul (KR)

( * ) Notice: Subject to any disclaimer, the term of this patent is extended or adjusted under 35 U.S.C. 154(b) by 0 days.

(21) Appl. No.: 13/491,823

(22) Filed: Jun. 8, 2012

(65) Prior Publication Data

US 2012/0316437 A1 Dec. 13, 2012

(30) Foreign Application Priority Data

Jun. 9, 2011 (KR) ........................ 10-2011-0055392

(51) Int. Cl.

*A61B 8/00* (2006.01)
*G10K 11/34* (2006.01)
*B06B 1/02* (2006.01)

(52) U.S. Cl.

CPC ............ *G10K 11/346* (2013.01); *B06B 1/0207* (2013.01); *B06B 2201/51* (2013.01)

(58) Field of Classification Search

CPC . B06B 1/0207; B06B 2201/51; G10K 11/346
See application file for complete search history.

(56) References Cited

U.S. PATENT DOCUMENTS 5,904,652 A 5/1999 Gilbert et al.
6,142,946 A 11/2000 Hwang et al.
7,775,979 B2 8/2010 Thomenius et al.
2005/0267369 A1 12/2005 Lazenby et al.
2006/0173305 A1 8/2006 Asafusa et al.
2009/0182233 A1 7/2009 Wodnicki (Continued)

FOREIGN PATENT DOCUMENTS

CN 2001-0024871 A 3/2001
CN 101745501 A 6/2010

(Continued)

OTHER PUBLICATIONS

Korean Office Action issued Apr. 3, 2014 in counterpart Korean Patent Application No. 10-2011-0055392 (35 pages, in Korean with English Translation).

Wodnicki, Robert, Charles G. Woychik, Albert T. Byun, Rayette Fisher, Kai Thomenius, Der-Song Lin, Xuefeng Zhuang, Omer Oralkan, Srikant Viathilingam, and Butrus T. Khuri-Yakub. "Multi-row linear cMUT array using CMUTs and mulitplexing electronics." In IEEE International Ultrasonics Symposium Proceedings, 2009, pp. 2696-2699.

(Continued)

*Primary Examiner* — Mark Remaly
(74) *Attorney, Agent, or Firm* — NSIP Law

(57) ABSTRACT

An apparatus for driving a two-dimensional transducer array, a medical imaging system and a method of driving a two-dimensional transducer array are provided. An apparatus for driving a two-dimensional (2D) transducer array including one or more transducers includes one or more drivers configured to respectively drive the transducers, each of the drivers including a register, a comparator, a pulse frequency setter, a multi-pulse controller, a transmission signal generator, a signal transceiver, a transmission and reception switch, and a reception signal amplifier, and a driving controller configured to control the drivers.

16 Claims, 8 Drawing Sheets

(56) References Cited

U.S. PATENT DOCUMENTS

| | | | | |
|---|---|---|---|---|
| 2010/0030081 | A1 * | 2/2010 | Masuzawa et al. | 600/459 |
| 2010/0152587 | A1 | 6/2010 | Haider et al. | |
| 2010/0168583 | A1 * | 7/2010 | Dausch et al. | 600/466 |
| 2011/0071397 | A1 * | 3/2011 | Wodnicki et al. | 600/459 |

FOREIGN PATENT DOCUMENTS

| | | | |
|---|---|---|---|
| CN | 101961249 | A | 2/2011 |
| EP | 0 464 440 | A2 | 6/1991 |
| JP | 2006-122188 | A | 5/2006 |
| JP | 2007-097760 | A | 4/2007 |
| KR | 20040069378 | A | 8/2004 |
| KR | 10-2006-0050773 | A | 5/2006 |
| KR | 10-2009-0006007 | A | 1/2009 |

OTHER PUBLICATIONS

Wygant, Ira O., et al. "Integration of 2D CMUT arrays with front-end electronics for volumetric ultrasound imaging." IEEE Transaction on Ultrasonics, Ferroelectronics and Frequency Control, 55.2 (Feb. 2008): pp. 327-342.

Extended European Search Report issued by the European Patent Office on Jan. 28, 2015 in corresponding European Application No. 12171476.0 (6 pages in English).

Chinese Office Action issued on May 6, 2015 in correspondence with Chinese Application No. 201210191844.X, along with an English Abstract (16 pages in English, 10 pages in Chinese.

* cited by examiner

APPARATUS FOR DRIVING TWO-DIMENSIONAL TRANSDUCER ARRAY, MEDICAL IMAGING SYSTEM, AND METHOD OF DRIVING TWO-DIMENSIONAL TRANSDUCER ARRAY

CROSS-REFERENCE TO RELATED APPLICATIONS

This application claims the benefit under 35 U.S.C. §119 (a) of Korean Patent Application No. 10-2011-0055392, filed on Jun. 9, 2011, in the Korean Intellectual Property Office, the entire disclosure of which is incorporated herein by reference for all purposes.

BACKGROUND

1. Field

The following description relates to an apparatus for driving a two-dimensional (2D) transducer array, a medical imaging system, and a method of driving a 2D transducer array.

2. Description of Related Art

A 2D transducer array includes m×n transducers and is used for beamform multiple channels to obtain a high resolution three-dimensional (3D) image. Here, the 2D transducer array is driven by a driving apparatus. In other words, the driving apparatus drives transducers to transmit and receive an ultrasonic signal respectively to and from a subject.

SUMMARY

In one general aspect, there is provided an apparatus for driving a two-dimensional (2D) transducer array including one or more transducers, the apparatus including one or more drivers configured to respectively drive the transducers, each of the drivers including a register, a comparator, a pulse frequency setter, a multi-pulse controller, a transmission signal generator, a signal transceiver, a transmission and reception switch, and a reception signal amplifier, and a driving controller configured to control the drivers.

The general aspect of the apparatus may further provide that the driving controller includes a memory, the memory being configured to store delay time control information and receiver transducer control information, the delay time control information being configured to control a delay time for transmission beamforming for each of the transducers, the receiver transducer control information being configured to select a receiver transducer from the transducers.

The general aspect of the apparatus may further provide that the memory is further configured to store, after the drivers transmit transmission signals to the transducers, delay time control information for following transmission beamforming and receiver transducer control information for selecting a following receiver transducer.

The general aspect of the apparatus may further provide that the drivers are further configured to perform processing operations with respect to reception signals that correspond to the transmitted transmission signals when the delay time control information for the following transmission beamforming and the receiver transducer control information for selecting the following receiver transducer are being stored in the memory.

The general aspect of the apparatus may further provide that the stored delay time control information and the stored receiver transducer control information are outputted in parallel in every column constituting the drivers or row constituting the drivers.

The general aspect of the apparatus may further provide that the register is configured to store delay time control information and receiver transducer control information, the delay time control information being configured to control a delay time for transmission beamforming for each of the transducers, the receiver transducer control information being configured to select a receiver transducer from the transducers.

The general aspect of the apparatus may further provide that the transmission and reception switch is turned on or off with reference to the receiver transducer control information.

The general aspect of the apparatus may further provide that the register is configured to output delay time control information, the comparator is configured to compare the outputted delay time control information with a reference code outputted from the driving controller, the pulse frequency setter is configured to set a pulse frequency for transmission beamforming if the outputted delay time control information is equal to the outputted reference code, and the multi-pulse controller is configured to control a number of pulses for the transmission beamforming if the outputted delay time control information is equal to the outputted reference code.

The general aspect of the apparatus may further provide that the transducers correspond to a capacitive Micromachined Ultrasonic Transducer (cMUT), and the drivers correspond to application specific integrated circuits (ASIC).

In another general aspect, there is provided an apparatus for driving a two-dimensional (2D) transducer array including one or more transducers, the apparatus including one or more drivers configured to respectively drive the transducers, and a memory configured to store delay time control information and receiver transducer control information, the delay time control information being configured to control a delay time for transmission beamforming for each of the transducers, the receiver transducer control information being configured to select a receiver transducer from among the transducers. The memory is further configured to store, after the drivers transmit transmission signals to the transducers, delay time control information configured to control a delay time for following transmission beamforming for each of the transducers and receiver transducer control information configured to select a following receiver transducer from the transducers.

The general aspect of the apparatus may further provide that the stored delay time control information configured to control the delay time for transmission beamforming for each of the transducers and the stored receiver transducer control information configured to select the receiver transducer from among the transducers are outputted in parallel in every column constituting the drivers or row constituting the drivers.

The general aspect of the apparatus may further provide that each of the drivers includes a register, a comparator, a pulse frequency setter, a multi-pulse controller, a transmission signal generator, a signal transceiver, a transmission and reception switch, and a reception signal amplifier.

The general aspect of the apparatus may further provide that the register is further configured to output the receiver transducer control information configured to select the receiver transducer from among the transducers, and the transmission and reception switch is turned on or off according to the outputted receiver transducer control information.

In yet another general aspect, there is provided a medical imaging system, including a probe including a driving apparatus and a front end processing apparatus, the driving apparatus being configured to drive a two-dimensional (2D) transducer array comprising one or more transducers, the front end processing apparatus being configured to process reception signals outputted from the driving apparatus, the driving apparatus including one or more drivers configured to respectively drive the transducers, each of the drivers including a register, a comparator, a pulse frequency setter, a multi-pulse controller, a transmission signal generator, a signal transceiver, a transmission and reception switch, and a reception signal amplifier, and a main system configured to synthesize the reception signals outputted from the probe.

The general aspect of the medical imaging system may further provide that the driving apparatus further includes a memory, the memory being configured to store delay time control information and receiver transducer control information, the delay time control information being configured to control a delay time for transmission beamforming for each of the transducers, the receiver transducer control information being configured to select a receiver transducer from the transducers.

The general aspect of the medical imaging system may further provide that the memory is further configured to store, after the drivers transmit transmission signals to the transducers, delay time control information configured to control a delay time for following transmission beamforming for each of the transducers and receiver transducer control information configured to select a following receiver transducer from the transducers.

In still another general aspect, there is provided a method of driving a two-dimensional (2D) transducer array including one or more transducers, the method including transmitting delay time control information and receiver transducer control information stored in a memory of a driving controller of a driving apparatus to respective registers of one or more drivers of the driving apparatus, outputting the transmitted delay time control information and the transmitted receiver transducer control information from the registers, comparing the outputted delay time control information with a reference code outputted from the driving controller, transmitting a transmission signal from one of the transducers corresponding to one of the drivers including compared delay time control information that is equal to the outputted reference code, receiving reception signals from the transducers, processing the received reception signals with reference to the outputted receiver transducer control information, and, when the receiving of the reception signals, the processing of the reception signals, or a combination thereof is performed, storing delay time control information configured to control a delay time for following transmission beamforming for each of the transducers and receiver transducer control information configured to select a following receiver transducer from the transducers in the memory.

The general aspect of the method may further provide that the transmitting of the delay time control information and the receiver transducer control information includes outputting the stored delay time control information and the stored receiver transducer control information in parallel in every column constituting the drivers or row constituting the drivers.

The general aspect of the method may further provide that the drivers respectively drive the transducers, and each of the drivers includes one of the respective registers, a comparator, a pulse frequency setter, a multi-pulse controller, a transmission signal generator, a signal transceiver, a transmission and reception switch, and a reception signal amplifier.

In a further general aspect, there is provided a non-transitory computer-readable recording medium having embodied thereon a computer program for executing a method of driving a two-dimensional (2D) transducer array including one or more transducers.

Other features and aspects may be apparent from the following detailed description, the drawings, and the claims.

Figure 1:
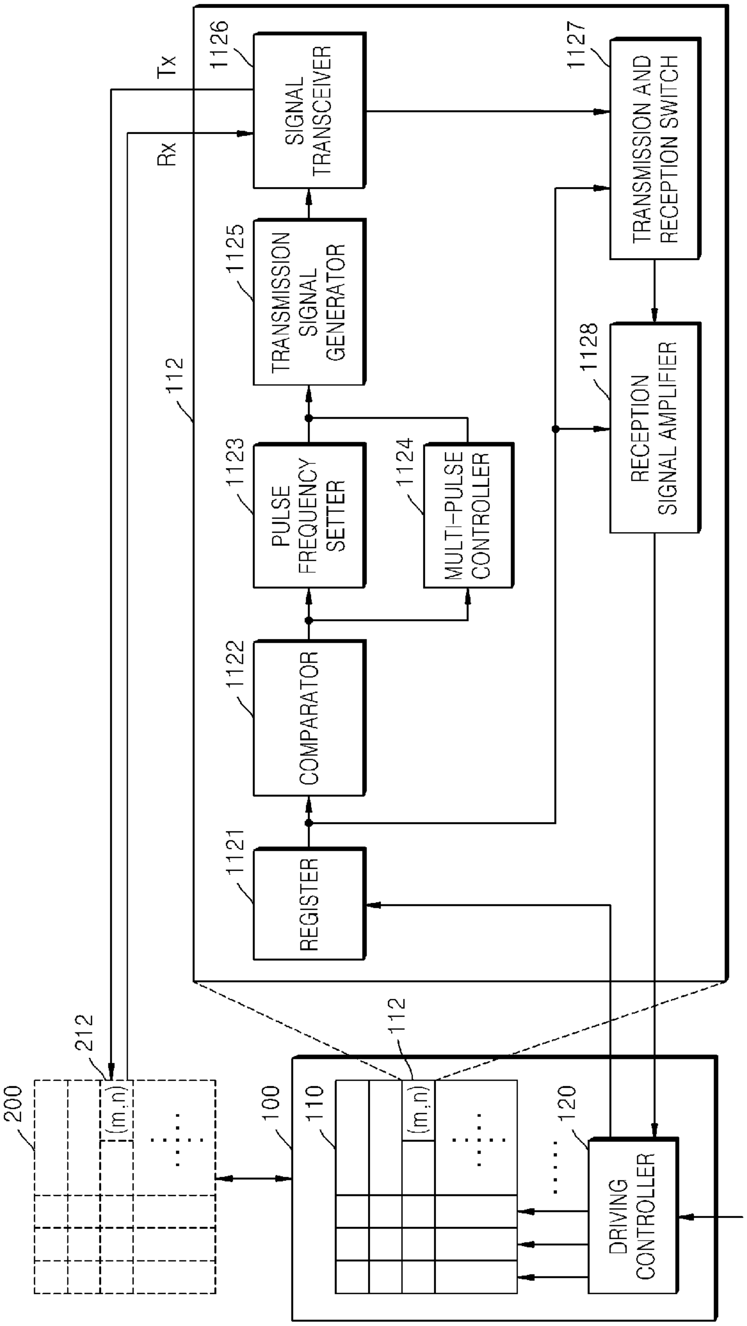
FIG. 1 is a block diagram illustrating a driving apparatus according to an example embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. In addition, descriptions of well-known functions and constructions may be omitted for increased clarity and conciseness.

FIG. 1 is a block diagram illustrating a driving apparatus 100 according to an example embodiment. Referring to FIG. 1, the driving apparatus 100 includes one or more drivers 110 and a driving controller 120. One 112 of the drivers 110 includes a register 1121, a comparator 1122, a pulse frequency setter 1123, a multi-pulse controller 1124, a transmission signal generator 1125, a signal transceiver 1126, a transmission and reception switch 1127, and a reception signal amplifier 1128. Other general-use elements may be further included in the driving apparatus 100 besides those described with respect to FIG. 1.

In the example embodiment, the drivers 110, the driving controller 120, the register 1121, the comparator 1122, the pulse frequency setter 1123, the multi-pulse controller 1124, the signal transceiver 1126, the transmission and reception switch 1127, and the reception signal amplifier 1128 of FIG. 1 may include one or more processors. The processors are an array of a plurality of logic gates, a combination of a general-purpose microprocessor and memory storing a program to be executed by the processor, or the like.

The driving apparatus 100 according to the example embodiment drives a two-dimensional (2D) transducer array 200. For example, the driving apparatus 100 transmits a transmission signal to the 2D transducer array 200 to drive the 2D transducer array 200, or receives a reception signal from the 2D transducer array 200. In the example embodiment, the reception signal is an echo signal reflected from a subject or the like. In the example embodiment, the subject is a portion of a human being, such as, but not limited to, a breast, a liver, an abdomen, or the like.

The drivers 110 according to the example embodiment respectively correspond to transducers included in the 2D transducer array 200. Therefore, the drivers 110 drive the transducers on a one-to-one basis. For example, the drivers 110 are formed of m rows and n columns. The drivers 110 are arrayed to drive the 2D transducer array 200 formed of m rows and n columns. Therefore, the driver 112 positioned in (m,n) drives a corresponding transducer 212 of the 2D transducer array 200 positioned in (m,n). As a result, in order to drive the 2D transducer array 200, a number of the drivers 110 provided is equal to a number of transducers included in the 2D transducer array 200.

Hereinafter, the driver 112 is described. The driver 112 corresponds to each of the drivers 110. As such, descriptions of each of the drivers 110 will be omitted.

For example, as shown in FIG. 1, the driver 112 includes the register 1121, the comparator 1122, the pulse frequency setter 1123, the multi-pulse controller 1124, the transmission signal generator 1125, the signal transceiver 1126, the transmission and reception switch 1127, and the reception signal amplifier 1128. Accordingly, since units for driving the 2D transducer array 200 are integrated into the driver 112, the drivers 110 are independently driven.

In addition, the reception signal amplifier 1128 is included in the driver 112 to process a reception signal. For example, if the 2D transducer array 200 is one of a plurality of 2D transducer arrays connected to each other for extension thereof, the drivers 110 extend to correspond to the extended 2D transducer arrays. Here, if the drivers 110 that are extended process the reception signal, the drivers 110 become affected by external noise since the drivers 110 are connected to each other. Thus, the image generated using the reception signal received in the driving apparatus 100 may have a deteriorated quality. Therefore, each of the drivers 110 includes the reception signal amplifier 1128, which performs an amplifying operation with respect to the reception signal.

Further, in the example embodiment, the 2D transducer array 200 may be a capacitive Micromachined Ultrasonic Transducer (cMUT) or the like. In addition, in the example embodiment, the driving apparatus 100 may be an application specific integrated circuit (ASIC) or the like. In other words, in the example embodiment, the cMUT may be made using Micro Electro Mechanical Systems (MEMS) technology or the like.

The drivers 110 according to the example embodiment respectively drive each of the transducers included in the 2D transducer array 200. The driving controller 120 controls the drivers 110. Each of the drivers 110 includes the register 1121, the comparator 1122, the pulse frequency setter 1123, the multi-pulse controller 1124, the transmission signal generator 1125, the signal transceiver 1126, the transmission and reception switch 1127, and the reception signal amplifier 1128.

The register 1121 stores pieces of control information. For example, the register 1121 stores delay time control information, receiver transducer control information, or a combination thereof. Here, the delay time control information is to control a delay time for transmission beamforming for each of the transducers, and the receiver transducer control information is to select a receiver transducer from the transducers. In the example embodiment, the delay time control information and the receiver transducer control information stored in the register 1121 is outputted from the driving controller 120 and stored in the register 1121.

For example, the register 1121 according to the example embodiment may be an N-bit shift register. Here, N may be a natural number greater than or equal to one. In this case, the delay time control information may be implemented by (N−1) bits, and the receiver transducer control information may be implemented by 1 bit.

The delay time control information includes information to control a delay time of a transmission signal transmitted from the driver 112 to the transducer 212. As such, the delay time control information may be information to control a delay time of a transmission signal transmitted from the transducer 212 to the subject. In addition, the delay time control information according to the example embodiment may be a delay time control code.

The receiver transducer control information includes information to select a receiver transducer from the transducers included in the 2D transducer array 200. For example, the receiver transducer control information includes information to select whether to receive a reception signal received by the transducer 212. As a result, reception beamforming may be performed with respect to a reception signal received by a transducer that is selected from the transducers included in the 2D transducer array 200 according to the receiver transducer control information. The delay time control information and the receiver transducer control information stored in the register 1121 are discussed further with reference to FIG. 3.

The comparator 1122 compares the delay time control information outputted from the register 1121 with a reference code outputted from the driving controller 120. Here, the reference code may be outputted from the driving controller 120 and then may be input into the comparator 1122 directly or through the register 1121. For example, the reference code may be a reference counter to transmit the transmission signal.

The comparator 1122 compares the delay time control information outputted from the register 1121 with the reference code to generate transmission pulse timing. For example, if the delay time control information outputted from the register 1121 is equal to the reference code according to the comparison result of the comparator 1122, the comparator 1122 controls the pulse frequency setter 1123 and the multi-pulse controller 1124 to respectively perform pulse frequency setting and multi-pulse control for generation of the transmission signal. If the delay time control information outputted from the register 1121 is not equal to the reference code according to the comparison result of the comparator 1122, the driver 112 does not transmit the transmission signal to the transducer 212. Therefore, the comparator 1122 controls a timing of the transmission signal transmitted from the driver 112 to the transducer 212. As a result, the driver 112 generates a transmission signal for which a delay time is implemented for transmission beamforming.

As shown in FIG. 1, the register 1121 and the comparator 1122 according to the example embodiment are installed as separate units. However, the register 1121 and the comparator

1122 may be integrated into one unit that performs operations of the register 1121 and the comparator 1122.

If the delay time control information is equal to the reference code according to the comparison result of the comparator 1122, the pulse frequency setter 1123 sets a pulse frequency for transmission beamforming. Here, the pulse frequency setter 1123 may set the pulse frequency according to pulse frequency control data. Pulse frequency control data may be outputted from the driving controller 120 and then may be input into the pulse frequency setter 1123 directly or through the register 1121. The pulse frequency setter 1123 according to the example embodiment may be a digital one-shot circuit or the like.

If the delay time control information is equal to the reference code according to the comparison result of the comparator 1122, the multi-pulse controller 1124 controls the number of pulses for transmission beamforming. Here, the multi-pulse controller 1124 may control the number of pulses that are generated under the same conditions according to pulse number control data. Pulse number control data may be outputted from the driving controller 120 and then may be input into the multi-pulse controller 1124 directly or through the register 1121. The multi-pulse controller 1124 may be a control block that controls the output of pulses as a train. The multi-pulse controller 1124 according to the example embodiment may be a pulse train controller but is not limited thereto.

As shown in FIG. 1, the register 1121, the comparator 1122, the pulse frequency setter 1123, and the multi-pulse controller 1124 are installed as separate units. However, the register 1121, the comparator 1122, the pulse frequency setter 1123, and the multi-pulse controller 1124 may be integrated into one control block or one unit that performs delay time control for transmission beamforming, control of whether a reception operation is to be performed, frequency setting for transmission beamforming, and pulse number control for transmission beamforming.

The transmission signal generator 1125 generates a transmission signal according to a predetermined number of pulses having a predetermined frequency under control of the multi-pulse controller 1124 and the pulse frequency setter 1123, respectively. For example, the transmission signal generator 1125 may be an analog high voltage circuit or the like that generates a high voltage pulse ranging from about 50 V to about 120 V to transmit to the transducer 112. The transmission signal generator 1125 according to the example embodiment may be a high voltage pulser including a high voltage metal oxide semiconductor (MOS) or the like.

The signal transceiver 1126 transmits the transmission signal generated by the transmission signal generator 1125 to the transducer 212 and receives a reception signal from the transducer 212. Here, the reception signal received from the transducer 212 may be an echo signal reflected from the subject. The signal transceiver 1126 according to the example embodiment may be a cMUT pad or the like that is connected to the transmission signal generator 1125 and transmits and receives a signal with the transducer 212.

The transmission and reception switch 1127 is turned on or off with reference to the receiver transducer control information outputted from the register 1121. In other words, if reception beamforming is performed with respect to the reception signal, the transmission and reception switch 1127 transmits the reception signal received from the signal transceiver 1126 to the reception signal amplifier 1128.

For example, if the receiver transducer control information indicates that receiving of the reception signal received from the transducer 212 is performed, the transmission and reception switch 1127 is turned on. If the receiver transducer control information indicates that receiving of the reception signal received from the transducer 212 is not performed, the transmission and reception switch 1127 is turned off. The transmission and reception switch 1127 according to the example embodiment may be a protection circuit, a protection switch, or the like.

The reception signal amplifier 1128 amplifies the reception signal outputted from the transmission and reception switch 1127. The reception signal amplifier 1128 according to the example embodiment may be a preamplifier or the like.

The reception signal amplified by the reception signal amplifier 1128 may be stored in an output buffer (illustrated as 128 in FIG. 2) to be transmitted to a front end processing apparatus (illustrated as 300 in FIG. 2) that controls the driving apparatus 100. The front end processing apparatus according to the example embodiment may be installed outside the driving apparatus 100, but is not limited thereto. The output buffer according to the example embodiment may be installed in the driving controller 120, but is not limited thereto.

Therefore, each of the drivers 110 according to the example embodiment includes a device or a unit for respectively driving the transducers included in the 2D transducer array 200. In other words, the register 1121, the comparator 1122, the pulse frequency setter 1123, the multi-pulse controller 1124, the transmission signal generator 125, the signal transceiver 1126, the transmission and reception switch 1127, and the reception signal amplifier 1128 are integrated into the driver 112. Therefore, the drivers 110 are connected in a tile form.

In addition, according to architecture of the example embodiment of the driving apparatus 100, each channel of the 2D transducer array 200 is individually controlled. In other words, the driving apparatus 100 gives a transmission pulse delay time for beamforming a predetermined position of the subject to each channel. Further, the driving apparatus 100 sets a frequency of a transmission pulse with respect to each channel and sets whether to perform a reception operation for reception beamforming with respect to each channel.

Figure 2:
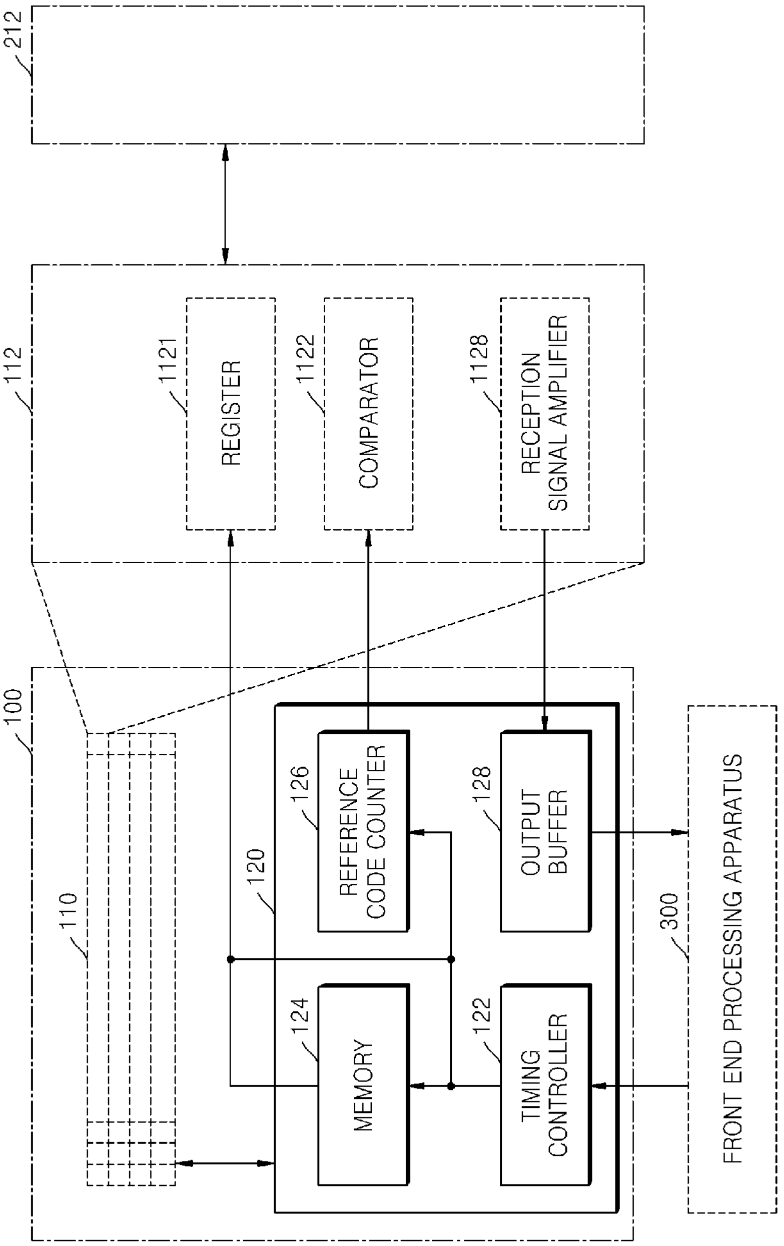
FIG. 2 is a block diagram illustrating a driving controller of the driving apparatus of FIG. 1 according to an example embodiment.

FIG. 2 is a block diagram illustrating the driving controller 120 of the driving apparatus 100 of FIG. 1 according to an example embodiment. Referring to FIG. 2, the driving controller 120 includes a timing controller 122, a memory 124, a reference code counter 126, and an output buffer 128. Other general-use elements may be further included in the driving controller 120 besides those described with respect to FIG. 2. In addition, the timing controller 122 and the reference code counter 126 of FIG. 2 may be one or more processors.

The driving controller 120 controls the drivers 110 to control all channels of the 2D transducer array 200. In other words, the driving controller 120 controls the drivers 110 so that the drivers 110 drive the 2D transducer array 200.

The timing controller 122 outputs a control signal to the drivers 110, the memory 124, and the reference code counter 126. Here, the control signal is outputted from a front end control apparatus 300 to control the driving apparatus 100. In addition, the timing controller 122 may generate a control signal to control the driving apparatus 100 and output the control signal to the drivers 110, the memory 124, and the reference code counter 126.

For example, the control signal to control the driving apparatus 100 may include a clock to control timing, delay time control information to control a delay time for transmission beamforming for each of the transducers included in the 2D transducer array 200, receiver transducer control information to select a receiver transducer from among the transducers included in the 2D transducer array 200, information regarding a pulse frequency for transmission beamforming, information regarding the number of pulses for transmission beamforming, or any combination thereof.

Here, the front end processing apparatus 300 may be an analog front end board (FEB) or the like.

The memory 124 stores the delay time control information, the receiver transducer control information, the information regarding the pulse frequency, the information regarding the number of pulses, or any combination thereof. In addition, the delay time control information, the receiver transducer control information, the information regarding the pulse frequency, and the information regarding the number of pulses may be outputted from the timing controller 122 and stored in the memory 124.

The memory 124 according to the example embodiment may be a static random access memory (SRAM) or the like. The memory 124 may be a general storage medium that includes a hard disk drive (HDD), a read only memory (ROM), a random access memory (RAM), a flash memory, and a memory card.

The memory 124 transmits the delay time control information and the receiver transducer control information to the register 1121, transmits the information regarding the pulse frequency to the pulse frequency setter 1123 directly or through the register 1121, and transmits the information regarding the number of pulses to the multi-pulse controller 1124 directly or through the register 1121.

Hereinafter, for descriptive convenience, the delay time control information, the receiver transducer control information, the information regarding the pulse frequency, and the information regarding the number of pulses will be referred to as transmission and reception beamforming control information. For example, the memory 124 may store transmission and reception beamforming control information for all of the transducers of the 2D transducer array 200.

In order to drive the m×n 2D transducer array 200, the m×n drivers 110 are installed. The memory 124 stores transmission and reception beamforming control information for a (1,1) transducer, transmission and reception beamforming control information for a (1,2) transducer, . . . , and transmission and reception beamforming control information for a (m,n) transducer.

In this case, the memory 124 transmits the transmission and reception beamforming control information for the (1,1) transducer to the (1,1) driver and the transmission and reception beamforming control information for the (1,2) transducer to the (1,2) driver and so on. According to this method, the memory 124 transmits the transmission and reception beamforming control information for the (m,n) transducer to the (m,n) driver. Therefore, the memory 124 may transmit transmission and reception beamforming control information to control the transducer 212 to the driver 112 that drives the transducer 212.

In addition, the transmission and reception beamforming control information stored in the memory 124 is outputted in parallel in every column constituting the drivers 110 or in every row constituting the drivers 110. Here, the parallel output in every column indicates that data outputting operations are simultaneously performed in each of a plurality of columns, and the parallel output in every row indicates that data outputting operations are simultaneously performed in each of a plurality of rows. For example, the data outputting operations may be loading operations or the like. A method of transmitting the transmission and reception beamforming control information from the memory 124 to the drivers 110 will be described with reference to FIG. 4.

The memory 124 also receives the transmission and reception beamforming control information from the front end processing apparatus 300 through the timing controller 122, stores the transmission and reception beamforming control information, and outputs the transmission and reception beamforming control information to the drivers 110.

Here, the transmission signal is transmitted from the drivers 110 to the 2D transducer array 200. Following transmission and reception beamforming control information is then stored in the memory 124. For example, when the following transmission and reception beamforming control information is being stored in the memory 124, the driving apparatus 100 performs a processing operation with respect to a reception signal corresponding to the transmission signal transmitted from the drivers 110. This will be described later with reference to FIG. 5.

The reference code counter 126 generates the reference code and transmits the reference code to each of the drivers 110. In other words, since the reference code counter 126 generates one reference code and transmits the reference code to the comparator 1122 of each of the drivers 110, the comparators 1122 of the drivers 110 share the same reference code. The reference code counter 126 according to the example embodiment may be a gray code counter or the like.

The comparator 1122 compares the delay time control information stored in the register 1121 with the reference code. In addition, if the delay time control information is equal to the reference code according to the comparison result, the driver 112 drives the transducer 212 to transmit the transmission signal to the subject. Therefore, the driving controller 120 implements delay time of the each transducers included in the 2D transducer array 200 by using the reference code generated by the reference code counter 126.

The output buffer 128 stores the amplified reception signals respectively outputted from the drivers 110 and outputs the amplified reception signals to the front end processing apparatus 300. The front end processing apparatus 300 according to the present embodiment receives the amplified reception signals from the output buffer 128 and performs a predetermined processing operation with respect to the amplified reception signals.

Figure 3:
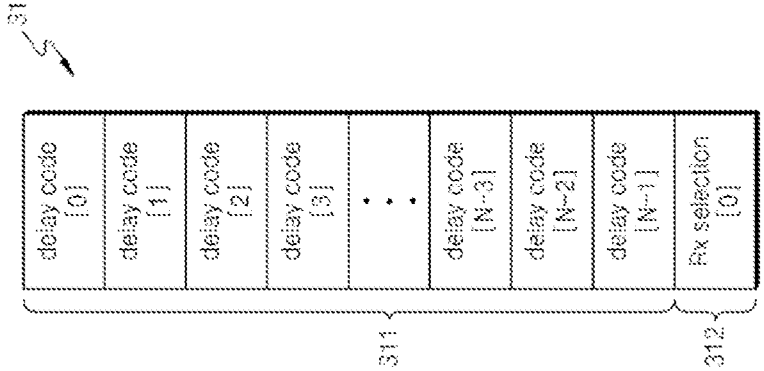
FIG. 3 is a view illustrating delay time control information and receiver transducer control information according to an example embodiment.

FIG. 3 is a view illustrating delay time control information 311 and receiver transducer control information 312 according to an example embodiment. Referring to FIG. 3, an N-bit shift register 31, which is an example of the register 1121 of FIGS. 1 and 2, is shown. The N-bit shift register 31 stores the delay time control information 311 and the receiver transducer control information 312 outputted from the memory 124. Here, the delay time control information 311 is implemented by (N−1) bits, and the receiver transducer control information is implemented by 1 bit.

The delay time control information 311 is generated by the front end processing apparatus 300 and then transmitted to the register 1121 sequentially through the timing controller 122 and the memory 124. Here, the delay time control information 311 is generated in a minimum unit of a period of a main clock. The main clock according to the example embodiment may be a clock to control a timing output from the timing controller 122 or the like. Here, the main clock is 200 MHz, and the delay time control information 311 is implemented by 11 bits. If the main clock is 200 MHz, the period of the main clock is 5 nanoseconds. In this case, the delay time control information 311 may control a delay time in a range between about 5 nanoseconds and about 10 microseconds.

In other words, if the period of the main clock is t seconds, and the delay time control information 311 is implemented by n bits, a maximum delay time controllable by the delay time control information 311 may be calculated in Equation 1, $$D_{Max}=t\times 2^n, \quad \text{[Equation 1]}$$

where $D_{Max}$ denotes a maximum delay time controllable by the delay time control information 311, t denotes a period of the main clock, and n denotes a number of bits of the delay time control information 311. Therefore, the delay time control information 311 may control a delay time between t and $D_{Max}$.

A beam focusing angle for transmission beamforming, which is implementable by the driving apparatus 100, may be determined according to the maximum delay time and may determine a field area of a volume able to be generated in an image generated by transmission and reception beamforming. A spot size of a focus point of transmission beamforming, which is implementable by the driving apparatus 100, may be determined according to a minimum delay time and may maximize reception strength depending on beam focusing.

As described above, the period of the main clock or the number of bits of the delay time control information 311 is controlled to control a delay time of the transmission signal transmitted from the transducer 212, the beam focusing angle for transmission beamforming, and the reception strength depending on the beam focusing.

The receiver transducer control information 312 is 0 or 1. If the receiver transducer control information 312 is 0, the transmission and reception switch 1127 is turned off to not perform a reception operation with respect to the reception signal received by the transducer 212. If the receiver transducer control information 312 is 1, the transmission and reception switch 1127 is turned on to perform the reception operation with respect to the reception signal received by the transducer 212.

If a determination of whether to receive the reception signal received by the transducer 212 is performed using a row decoder or a column decoder, it is difficult to simultaneously transmit a plurality of reception signals to the outside. Therefore, it is difficult to extend the 2D transducer array 200. Therefore, the driving apparatus 100 according to the example embodiment determines whether to perform the reception operation with respect to the reception signal received by the transducer 212 by using the receiver transducer control information 312 without using the row decoder or the column decoder.

In other words, the front end processing apparatus 300 determines whether to perform the reception operation with respect to the reception signal received by the transducer 212. In addition, the receiver transducer control information 312 is transmitted from the front end processing apparatus 300 to the transmission and reception switch 1127 sequentially through the timing controller 122, the memory 124, and the register 1121 according to the determination. The transmission and reception switch 1127 is turned on or off with reference to the receiver transducer control information 312, thereby controlling whether to perform the reception operation with respect to the reception signal received by the transducer 212.

Figure 4:
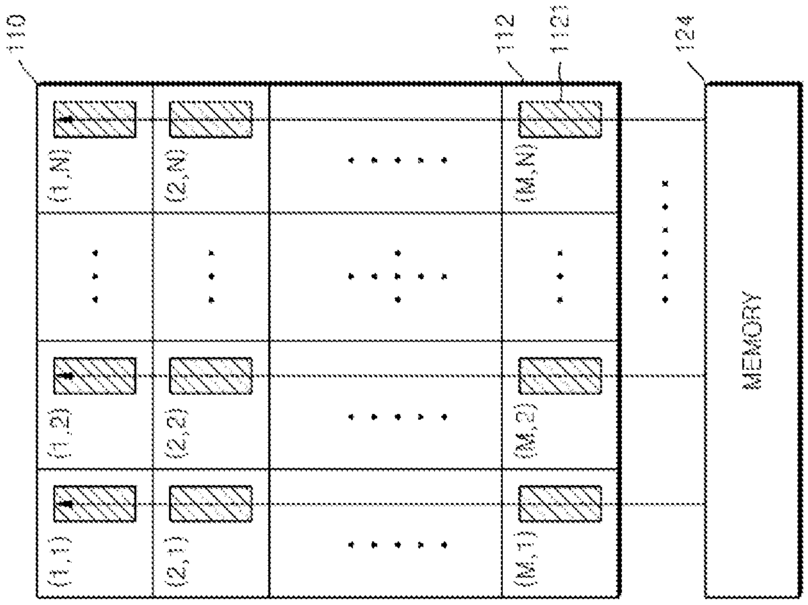
FIG. 4 is a view illustrating a method of transmitting transmission and reception beamforming control information from a memory to one or more drivers according to an example embodiment.

FIG. 4 is a view illustrating a method of transmitting transmission and reception beamforming control information from the memory 124 to the drivers 110 according to an example embodiment. The transmission and reception beamforming control information according to the example embodiment includes delay time control information, receiver transducer control information, information regarding a pulse frequency, information regarding the number of pulses, or any combination thereof. Hereafter, for descriptive convenience, an example of transmission and reception beamforming control information including the delay time control information and the receiver transducer control information is described. However, the information regarding the pulse frequency and the information regarding the number of pulses may be applied as well.

The delay time control information and the receiver transducer control information stored in the memory 124 according to the example embodiment are outputted in parallel in every column constituting the drivers 110 or in every row constituting the drivers 110.

An example of the M×N drivers 110 formed of M rows and N columns will be described with reference to FIG. 4. As shown in FIG. 4, each of the drivers 110 includes the register 1121. Therefore, the memory 124 outputs the delay time control information and the receiver transducer control information for each of the drivers 110 in the N columns in parallel.

The parallel output in the N columns according to the example embodiment indicates that the delay time control information and the receiver transducer control information in the each of N columns are simultaneously outputted. In other words, delay time control information and receiver transducer control information for a (1,1) driver, a (2,1) driver, . . . , and a (M,1) driver constituting a first column are sequentially outputted. Simultaneously, delay time control information and receiver transducer control information for a (1,2) driver, a (2,2) driver, . . . , and a (M,2) driver constituting a second column are sequentially outputted. In addition, according to the above method, delay time control information and receiver transducer control information for a (1,N) driver, a (2,N) driver, . . . , and a (M,N) driver constituting an $N^{th}$ column are sequentially outputted. The method for parallel outputting in every column is described with reference to FIG. 4, but a method for parallel outputting in every row may be applied.

Figure 5:
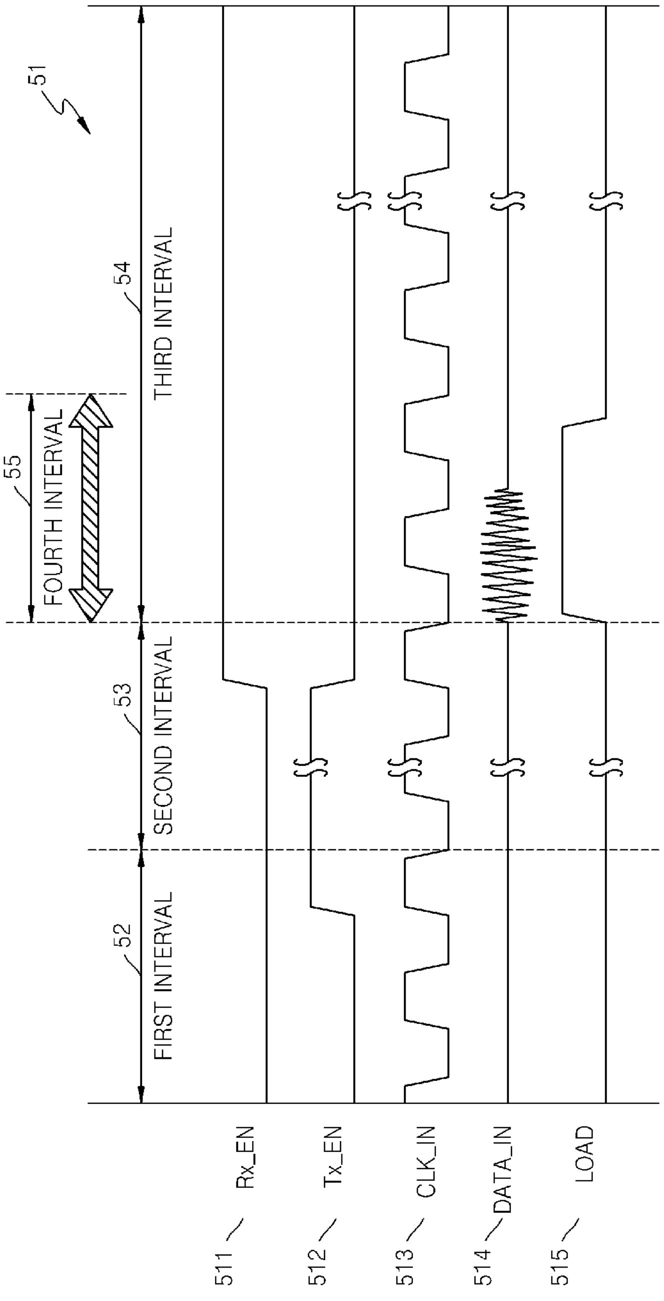
FIG. 5 is a timing diagram of the driving apparatus of FIG. 1 according to an example embodiment.

FIG. 5 is a timing diagram 51 of the driving apparatus 100 of FIG. 1 according to an example embodiment. Referring to FIG. 5, the timing diagram 51 shows timing flows of Rx_EN 511 enabling a receiver transducer, Tx_EN 512 enabling transmission beamforming, CLK_IN 513 indicating a clock, DATA_IN 514 indicating data, and LOAD 515 enabling data loading into the memory 124.

A first interval 52 indicates a time for transmission of data by the memory 124 to the registers 1121 included in the drivers 110. For example, as described with reference to FIG. 4, the delay time control information and the receiver transducer control information stored in the memory 124 are outputted in parallel to every column or every row constituting the drivers 110 for the first interval 52. Therefore, the first interval 52 may be considered a data loading time or the like.

A second interval 53 indicates a time for performing of transmission beamforming. For example, the second interval 53 indicates a time taken by the drivers 110 that respectively drive the transducers included in the 2D transducer array 200 to transmit the transmission signal to the subject. Therefore, the second interval 53 may be considered a transmission pulsing time or the like.

A third interval 54 indicates a time for performing a reception operation and reception beamforming. For example, the third interval 54 indicates a time taken by the drivers 110 and the front end processing apparatus 300 to process reception signals respectively received from the transducers included in the 2D transducer array 200. Therefore, the third interval 54 may be considered a reception read-out time or the like.

A fourth interval 55 indicates a time taken by the front end processing apparatus 300 to transmit data to the memory 124. Here, the data transmitted from the front end processing apparatus 300 to the memory 124 may be delay time control information for following transmission beamforming and receiver transducer control information for selecting a following receiver transducer. Therefore, the fourth interval 55 may be considered a memory loading time or the like.

As shown in FIG. 5, the fourth interval 55 is included in the third interval 54. In other words, the transmission of the data from the front end processing apparatus 300 to the memory 124 may be performed simultaneously with a reception operation and reception beamforming. Here, the simultaneous performance of the data transmission with the reception operation and the reception beamforming indicates that data may be transmitted from the front end processing apparatus 300 to the memory 124 at any time after transmission beamforming is ended.

In this case, ending of the transmission beamforming occurs after transmitting transmission signals from the transducers included in the 2D transducer array 200 to the subject. In other words, the time for which the reception operation and the reception beamforming is performed may include all of a time taken for a transmission signal transmitted from a transducer to reach a subject, a time taken for a reception signal reflected from the subject to reach the transducer, a time taken for the reception signal received by the transducer to be processed by the drivers 110, a time taken for reception signals outputted from the drivers 110 to be processed by the front end processing apparatus 300, and a time taken for the reception signals processed by the front end processing apparatus 300 to be reception-beamformed.

Therefore, after the drivers 110 transmit transmission signals to the 2D transducer array 200, delay time control information for following transmission beamforming and receiver transducer control information for selecting a following receiver transducer are stored in the memory 124.

Alternatively, when the delay time control information for the following transmission beamforming and the receiver transducer control information for selecting the following receiver transducer are being stored in the memory 124, the drivers 110 may perform processing operations with respect to reception signals corresponding to transmitted transmission signals.

For descriptive convenience, the fourth interval 55 starts simultaneously with the third interval 54 in FIG. 5, but is not limited thereto. Therefore, a data loading operation of the fourth interval 55 may be performed at any time corresponding to the third interval 54.

Hereinafter, delay time control information for following transmission beamforming and receiver transducer control information for selecting a following receiver transducer will be described.

The driving apparatus 100 according to the example embodiment may perform transmission and reception beamforming one or more times. In this case, the memory 124 stores delay time control information and receiver transducer control information for currently performed transmission and reception beamforming, and the drivers 110 perform transmission and reception beamforming with reference to the delay time control information stored in the memory 124. In addition, the drivers 110 turn off or on the transmission and reception switch 127 with reference to the receiver transducer control information stored in the memory 124.

Therefore, if the transmission beamforming is performed, and the transmission and reception switch 1127 is turned off or on, the drivers 110 no longer refer to the delay time control information and the receiver transducer control information stored in the memory 124. Accordingly, the delay time control information for the following transmission beamforming and the receive transducer control information for selecting the following receiver transducer is transmitted from the front end processing apparatus 300 to the memory 124 after the transmission beamforming is ended. As a result, the delay time control information for the following transmission beamforming and the receiver transducer control information for selecting the following receiver transducer are stored in the memory 124 after current transmission beamforming is ended. The data transmission from the front end processing apparatus 300 to the memory 124 may be performed through a pad, a low voltage differential signaling (LVDS) block, the timing controller 122, or the like.

The driving apparatus 100 uses an enormous amount of data to drive the 2D transducer array 200. This data is generated by the front end processing apparatus 300 and transmitted to the 2D transducer array 200 through the drivers 110.

Figure 6:
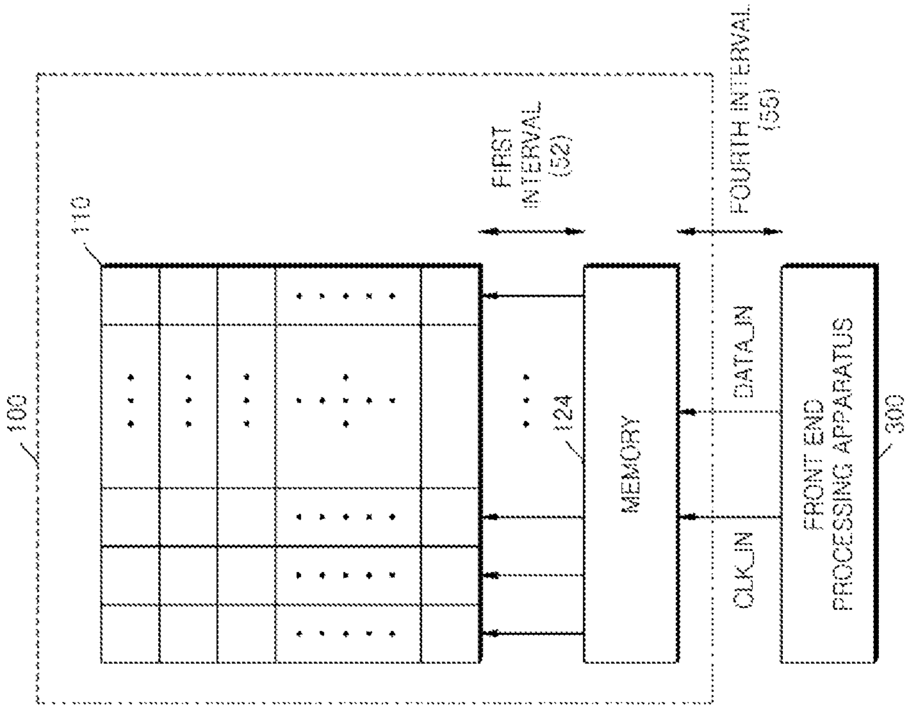
FIG. 6 is a block diagram illustrating a data loading time among a front end processing apparatus, a memory, and one or more drivers according to an example embodiment.

FIG. 6 is a block diagram illustrating a data loading time among the front end processing apparatus 300, the memory 124, and the drivers 110 according to an example embodiment. Referring to FIGS. 5 and 6, the front end processing apparatus 300 transmits a clock and data to the memory 124 for the fourth interval 55. In addition, the memory 124 transmits the data to the drivers 110 in parallel for the first interval 52. Here, the data may include delay time control information, receiver transducer control information, or the like.

Since the data transmission from the front end processing apparatus 300 to the memory 124 is performed in parallel as described above, a loading time of the first interval 52 is not long. A reception operation and reception beamforming may be simultaneously performed for the fourth interval 55. As a result, the fourth interval may take relatively longer than the first interval 52.

Therefore, the memory 124 according to the example embodiment stores delay time control information, receiver transducer control information, or the like, for all of the transducers included in the 2D transducer array 200. In addition, data transmissions from the memory 124 to the drivers 110 according to the example embodiment are performed in parallel. Accordingly, if the drivers 110 are constituted in M columns, a loading time may be reduced by 1/M times due to the use of the memory 124.

Figure 7:
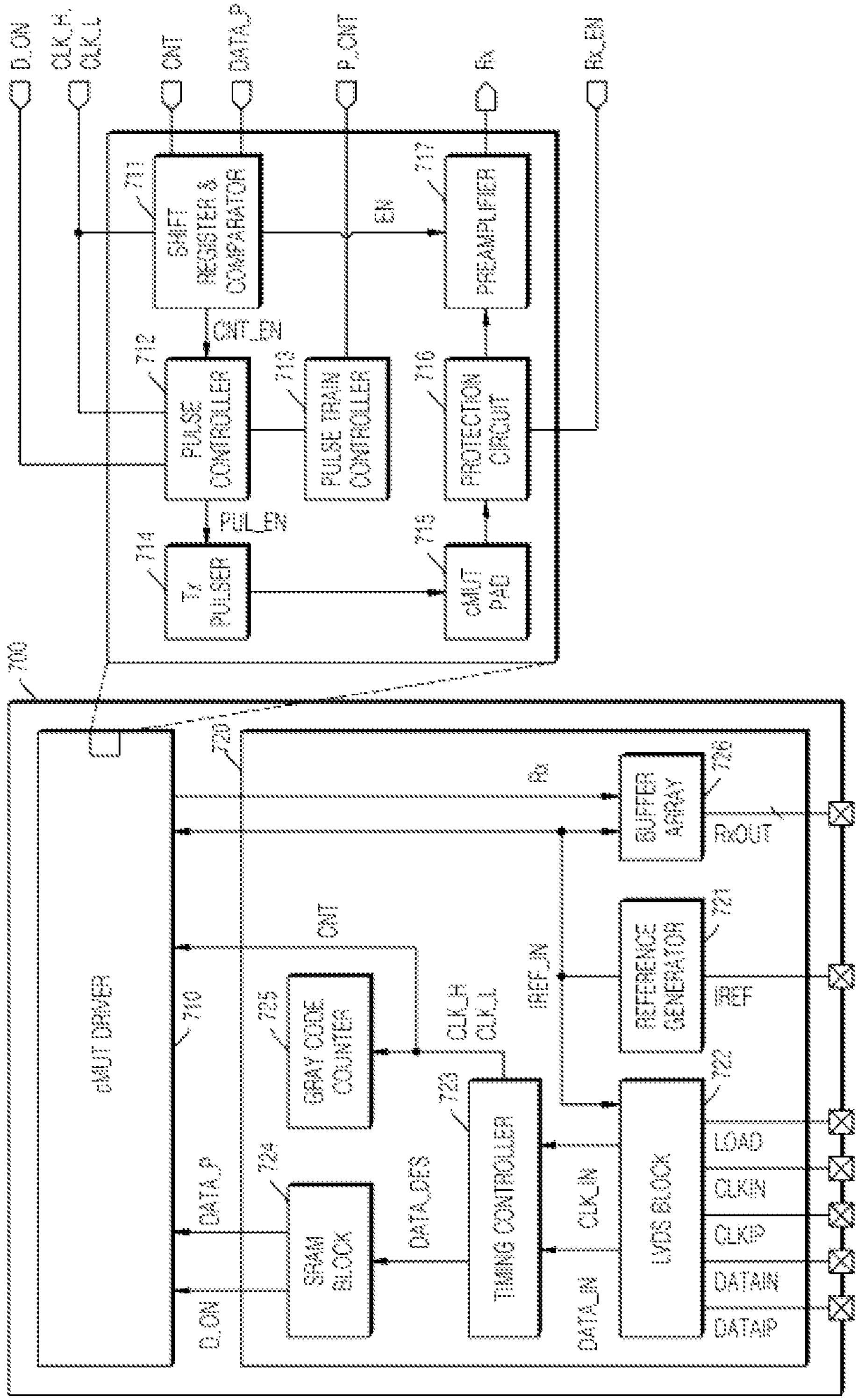
FIG. 7 is a block diagram illustrating a driving apparatus of FIG. 1 implemented as an application specific integrated circuit (ASIC) according to an example embodiment.

FIG. 7 is a block diagram illustrating the driving apparatus 100 of FIG. 1 implemented as an application specific integrated circuit (ASIC) 700 according to an example embodiment. The ASIC 700 of FIG. 7 corresponds to an example embodiment of the driving apparatus 100 of FIG. 1. Therefore, the driving apparatus 100 is not limited to units shown in FIG. 7. In addition, contents described in relation to FIGS. 1-6 are applied to the ASIC 700 of FIG. 7, and thus repeated descriptions will be omitted.

The ASIC 700 includes a cMUT driver 710 and a driving controller 720. Here, the cMUT driver 710 corresponds to an example of the drivers 110 of FIG. 1 and the driving controller 720 corresponds to an example of the driving controller 120 of FIG. 1, and thus repeated descriptions will be omitted.

The cMUT driver 710 includes a shift register and comparator 711, a pulse controller 712, a pulse train controller 713, a Tx pulser 714, a cMUT pad 715, a protection circuit 716, and a preamplifier 717.

The shift register & comparator 711 corresponds to an example of the register 1121 and the comparator 1122 of FIG. 1, and the pulse controller 712 corresponds to an example of the pulse frequency setter 1123 of FIG. 1. In addition, the pulse train controller 713 corresponds to an example of the multi-pulse controller 1124 of FIG. 1, and the Tx pulser 714 corresponds to an example of the transmission signal generator 1125 of FIG. 1. Further, the cMUT pad 715 corresponds to an example of the signal transceiver 1126 of FIG. 1. The protection circuit 716 corresponds to an example of the transmission and reception switch 1127 of FIG. 1, and the preamplifier 717 corresponds to an example of the reception signal amplifier 1128 of FIG. 1. Therefore, repeated descriptions will be omitted.

The driving controller 720 includes a reference generator 721, a LVDS block 722, a timing controller 723, an SRAM block 724, a gray code counter 725, and a buffer array 726.

The reference generator 721 is connected to a front end controller (not shown) to generate a reference, and the LVDS block 722 is connected to the front end controller to transmit data and a clock. Here, LVDS indicates a way to achieve high-speed data communication.

The timing controller 723 corresponds to an example of the timing controller 122 of FIG. 2 and controls a whole timing of the ASIC 700. The SRAM block 724 corresponds to an example of the memory 124 of FIG. 2, the gray code counter 725 corresponds to an example of the reference code counter 126 of FIG. 2, and the buffer array 726 corresponds to an example of the output buffer 128 of FIG. 2. Therefore, repeated descriptions will be omitted.

In FIG. 7, the pulse controller 712, the LVDS block 722, the timing controller 723, and the gray code counter 725 may be a 200 MHz operation block. In addition, the shift register & comparator 711, the pulse train controller 713, and the SRAM block 724 may be a 33.3 MHz operation block.

Signals shown in FIG. 7 will now be described in more detail. D_ON is a control bit for setting a frequency. If D_ON is implemented by n bits, $2^n$ frequencies are set. DATA_P indicates a delay code for transmission beamforming for each of a plurality of transducers and a receiver transducer control bit. P_CNT indicates a control bit for setting the number of transmission pulses. If P_CNT is implemented by n bits, $2^n$ pulses may be transmitted. Rx indicates an output node for outputting a reception signal. Rx_EN indicates a signal for controlling reception timing, and Tx_EN indicates a signal for controlling transmission timing. LOAD indicates a signal for loading data into the SRAM block 724. DATAIP and DATAIN indicate two input terminals for inputting data into the LVDS block 722, thereby outputting DATA_IN. CLKIN and CLKIP indicate two input terminals for inputting clocks into the LVDS block 722, thereby outputting CLK_IN. IREF indicates a reference current input node, and RxOUT indicates a reception signal output node.

Figure 8:
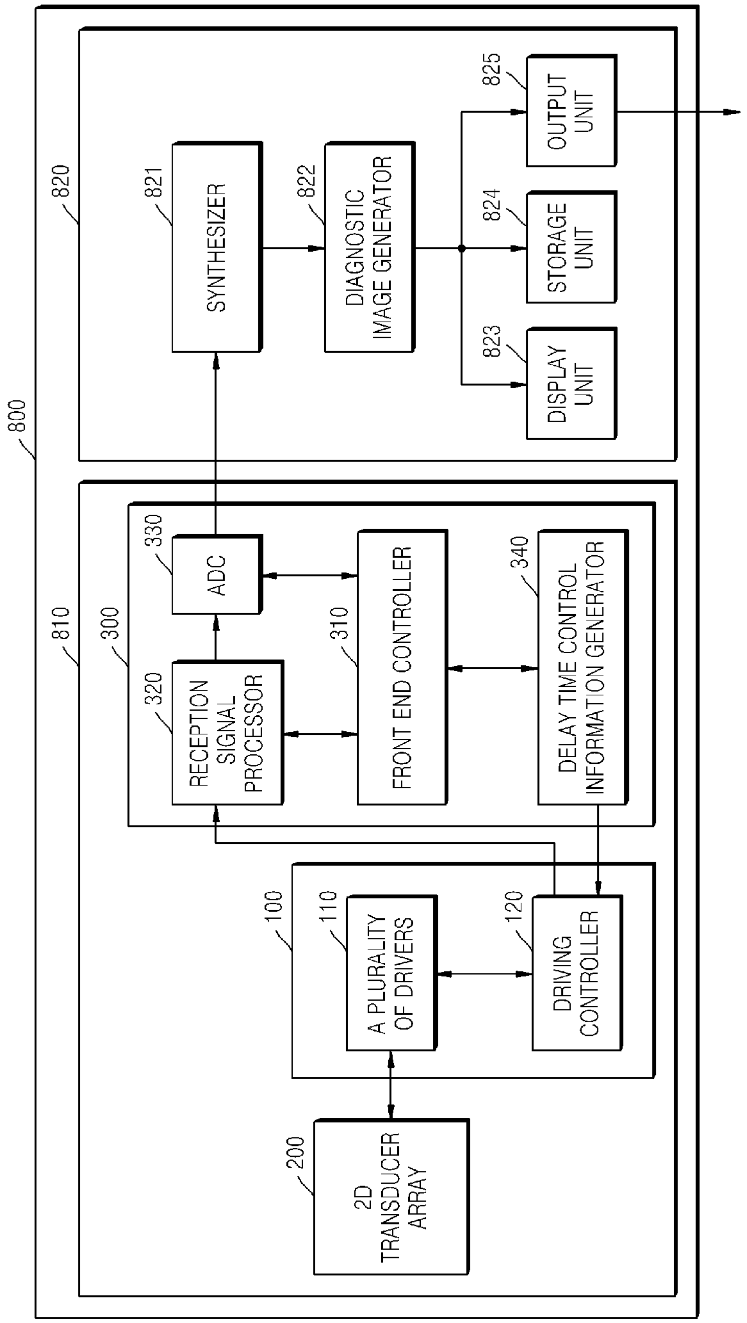
FIG. 8 is a block diagram of a medical imaging system according to an example embodiment.

FIG. 8 is a block diagram of a medical imaging system 800 according to an example embodiment. Referring to FIG. 8, the medical imaging system 800 includes a probe 810 and a main system 820. The probe 810 includes the driving apparatus 100 of FIG. 1, the 2D transducer array 200, and the front end processing apparatus 300. The driving apparatus 100 includes the drivers 110 and the driving controller 120. The front end processing apparatus 300 includes a front end controller 310, a reception signal processor 320, an analog-to-digital converter (ADC) 330, and a delay time control information generator 340. The main system 820 includes a synthesizer 821, a diagnostic image generator 822, a display unit 823, a storage unit 824, and an output unit 825.

The driving apparatus 100, the 2D transducer array 200, and the front end processing apparatus 300 of FIG. 8 respectively correspond to an example embodiment of the driving apparatus 100, the 2D transducer array 200, and the front end processing apparatus 300 of FIGS. 1 and 2. Therefore, contents described in relation to FIGS. 1-7 are applied to the medical imaging system 800 of FIG. 8. Thus, repeated descriptions will be omitted.

The medical imaging system 800 according to the example embodiment provides a diagnostic image of a subject. For example, the medical imaging system 800 displays a diagnostic image indicating a subject or outputs a signal indicating the diagnostic image of the subject to an external device that displays the diagnostic image indicating the subject. Here, the subject may be a portion of a human being, such as, but not limited to, a breast, a liver, an abdomen, or the like. In addition, the diagnostic image according to the present embodiment may be a three-dimensional (3D) ultrasonic image or the like.

The probe 810 includes the 2D transducer array 200, the driving apparatus 100 that drives the 2D transducer array 200, and the front end processing apparatus 300 that processes reception signals outputted from the driving apparatus 100.

The driving apparatus 100 includes the drivers 110 that respectively drive transducers included in the 2D transducer array 200 and the driving controller 120 that controls the drivers 110. In addition, each of the drivers 110 according to the example embodiment includes a register, a comparator, a pulse frequency setter, a multi-pulse controller, a transmission signal generator, a signal transceiver, a transmission and reception switch, and a reception signal amplifier.

The front end processing apparatus 300 processes the reception signals and generates delay time control information. Here, the reception signals are amplified reception signals outputted from the driving controller 120 of the driving apparatus 100. The delay time control information is information for controlling a delay time for transmission beamforming. In addition, the front end processing apparatus 300 according to the example embodiment may be an analog front end board (FEB) or the like.

The front end controller 310 controls the front end processing apparatus 300. For example, the front end controller 310 controls the reception signal processor 320 and the ADC 330 to process the reception signals and the delay time control information generator 340 to generate the delay time control information.

The front end controller 310 generates receiver transducer control information for selecting a receiver transducer from among the transducers included in the 2D transducer array 200, information regarding a pulse frequency for transmission beamforming, and information regarding the number of pulses for transmission beamforming. The receiver transducer control information, the information regarding the pulse frequency, and the information regarding the number of pulses that are generated by the front end controller 310 are transmitted to the driving controller 120 of the driving apparatus 100.

The reception signal processor 320 processes the amplified reception signals outputted from the driving controller 120 of the driving apparatus 100 according to a predetermined processing operation. For example, the reception signal processor 320 may include a low noise amplifier (LNA) (not shown), a variable gain amplifier (VGA) (not shown), an anti-aliasing filter (AAF) (not shown), or the like. The LNA reduces noise of an analog signal reflected from the subject, the VGA controls a gain value according to an input signal, and the AAF filters aliasing elements. Here, the VGA may be a time gain compensator (TGC) that compensates for a gain according to a distance to a focus point or the like.

The ADC 330 converts the processed reception signals outputted from the reception signal processor 320 into digital signals. One or more reception signal processors and one or more ADCs may be provided. For example, one or more reception signal processors and one or more ADCs may be provided according to the number of rows or columns of the drivers 110. In other words, m reception signal processors and m ADCs may be provided with respect to m rows of the drivers 110 or n reception signal processors and n ADCs may be provided with respect to n columns of the drivers 110.

The delay time control information generator 340 generates delay time control information for controlling a delay time for transmission beamforming. The delay time control information generator 340 according to the example embodiment may be a transmission beamformer or the like. The delay time control information generated by the delay time control information generator 340 is transmitted to the driving apparatus 100 and the synthesizer 821 of the main system 820. The delay time control information according to the example embodiment includes information regarding a delay time. The delay time is a time delay value for beamforming and, as an example, is calculated according to distance between the focus point of the subject and each of the transducers included in the 2D transducer array 200. As an example, the delay time control information generator 340 is included in the probe 810 in FIG. 8. However, the delay time control information generator 340 may be included in the main system 820.

The main system 820 synthesizes the reception signals outputted from the probe 810, and generates, displays, outputs, and stores the diagnostic image. The synthesizer 821 synthesizes the digital reception signals outputted from the probe 810. For example, the synthesizer 821 synthesizes the reception signals outputted from the probe 810 according to the delay time control information generated by the delay time control information generator 340. For example, the probe 810 outputs m reception signals corresponding to m rows or n reception signals corresponding to n columns. Thus, the synthesizer 821 synthesizes output reception signals into one signal. The synthesizer 821 according to the example embodiment is a reception beamformer or the like.

The diagnostic image generator 822 generates the diagnostic image by using the reception signal synthesized by the synthesizer 821. For example, the diagnostic image generator 822 may include a digital signal processor (DSP) (not shown) and a digital scan converter (DSC) (not shown). The DSP according to the example embodiment processes the reception signal synthesized by the synthesizer 821 to form image data that represents a b-mode (brightness-mode), a c-mode (color-mode), a d-mode (doppler-mode), or the like. The DSC generates a scan-converted diagnostic image to display the image data generated by the DSP.

The display unit 823 displays the diagnostic image generated by the diagnostic image generator 822. For example, the display unit 823 includes all of output units such as a display panel, a liquid crystal display (LCD) screen, a monitor, or the like installed in the medical imaging system 800. The medical imaging system 800 according to the example embodiment may not include the display unit 823 but may include the output unit 825 to output the diagnostic image generated by the diagnostic image generator 822 to an external display unit (not shown).

The storage unit 824 stores data generated when an operation of the medical imaging system 800 is performed. For example, the storage unit 824 stores the reception signals outputted from the probe 810, the image data representing the b-mode, the c-mode, the d-mode, or the like, or the scan-converted diagnostic image. The storage unit 824 according to the example embodiment may be a general storage medium including a hard disk drive (HDD), a ROM, a RAM, a flash memory, or a memory card.

The output unit 825 may transmit and receive data to and from an external device through a wired/wireless network or a wired serial communication. Here, a network includes the Internet, a local area network (LAN), a wireless LAN (WLAN), a wide area network (WAN), a personal area network (PAN), or other types of networks capable of transmitting and receiving information.

The storage unit 824 and the output unit 825 according to the present embodiment may further include image reading and searching functions to be integrated into a form such as a picture archiving communication system (PACS).

Figure 9:
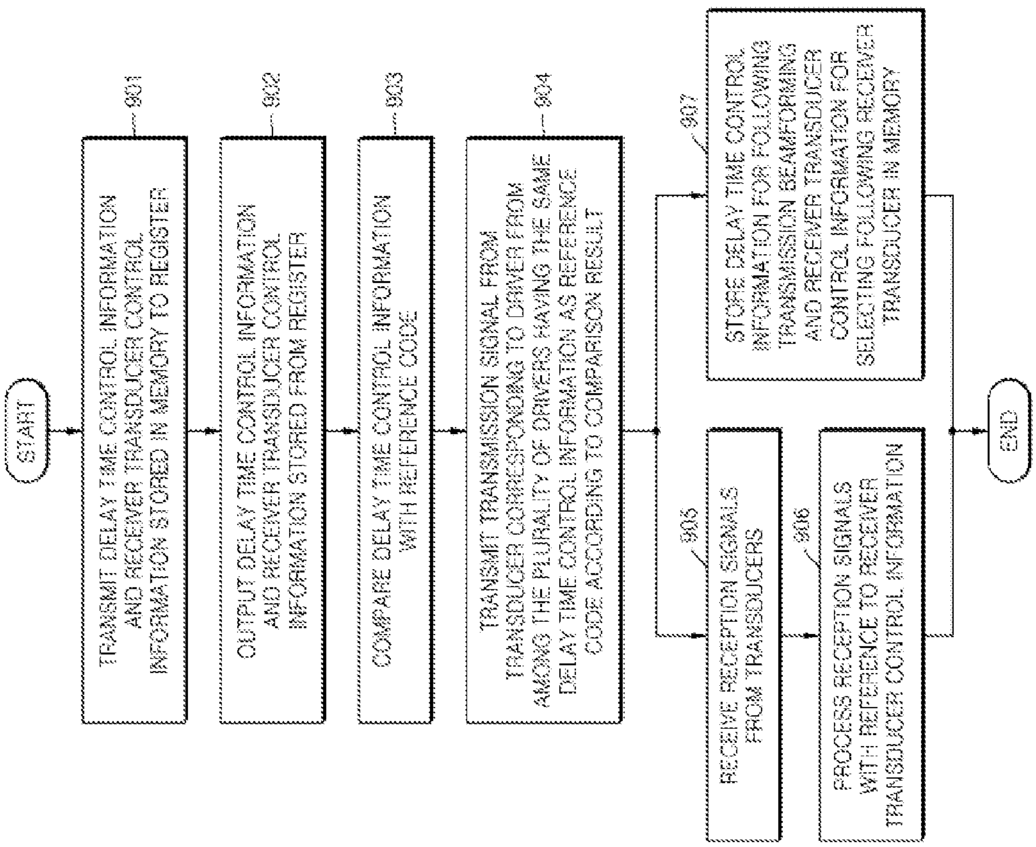
FIG. 9 is a flowchart illustrating a method of driving a 2-dimensional (2D) transducer array according to an example embodiment.

FIG. 9 is a flowchart illustrating a method of driving a 2D transducer array according to an example embodiment. Referring to FIG. 9, the method includes operations processed in the driving apparatus 100 or the medical imaging system 800 shown in FIGS. 1, 2, and 8. Therefore, although the above descriptions of the driving apparatus 100 or the medical imaging system 800 of FIGS. 1, 2, and 8 are omitted hereinafter, the above descriptions may be applied to the method of FIG. 9.

Delay time control information and receiver transducer control information stored in the memory 124 of the driving controller 120 are transmitted (901) to respective registers of one or more drivers 110. The transmitted delay time control information and the transmitted receiver transducer control information are outputted (902) from the registers. The outputted delay time control information is compared (903) with a reference code outputted from the driving controller 120. A transmission signal is transmitted (904) from one 212 of the transducers corresponding to one 112 of the drivers 110 having compared delay time control information that is equal to the outputted reference code. Reception signals are received (905) from the transducers. The received reception signals are processed (906) with reference to the outputted receiver transducer control information. When the receiving of the reception signals, the processing of the reception signals, or a combination thereof is performed, the delay time control information and the receiver transducer control information are stored (907) in the memory 124.

The flow chart of FIG. 9 will now be described with reference to the timing diagram of FIG. 5. The transmitting of the delay time control information and the receiver transducer control information (901) indicates the first interval 52 of FIG. 5, the comparing of the outputted delay time control information (903) and the transmitting of the transmission signal (904) indicate the second interval of FIG. 5, the receiving of the reception signals (905) and the processing of the received reception signals (906) indicate the third interval 54 of FIG. 5, and the storing of the delay time control information and the receiver transducer control information when the receiving of the reception signals, the processing of the reception signals, or a combination thereof is performed (906) indicates the fourth interval 55 of FIG. 5.

Accordingly to teachings above, there is provided an apparatus for driving a 2D transducer array including one or more transducers, in which the apparatus and a medical imaging system including the apparatus may easily be extended and integrated and may reduce a time necessary for beamforming of a subject and generation of a diagnostic image.

According to teachings above, there is provided an apparatus for driving a 2D transducer array including one or more transducers, in which units for driving the 2D transducer array are integrated into independently driven drivers that are connected in a tile form, which may serve to easily control the 2D transducer array and extend the 2D transducer array according to a shape of an aperture performing beamforming.

According to teachings above, there is provided an apparatus for driving a 2D transducer array including one or more transducers, in which a reception signal amplifier is included in each of drivers, which may serve to improve quality of an image generated using a reception signal received by the apparatus.

According to teachings above, there is provided an apparatus for driving a 2D transducer array including one or more transducers, in which the transducer array is a cMUT, which may serve to easily achieve multi-channel integration through a 2D array and, according to beamforming using the cMUT, enable a high resolution 3D image to be obtained.

According to teachings above, there is provided an apparatus for driving a 2D transducer array including one or more transducers, in which a transmission and reception switch transmits a reception signal received from a signal transceiver to a reception signal amplifier if reception beamforming is performed with respect to the reception signal, which may serve to prevent a high voltage transmission signal from affecting the reception signal amplifier.

According to teachings above, there is provided an apparatus for driving a 2D transducer array including one or more transducers, the apparatus simultaneously performing an operation to store transmission and reception beamforming control information in a memory and an operation performed after a transmission signal is transmitted from drivers, which may provide a reduction in time taken to load a large amount of transmission and reception beamforming control information into the drivers.

According to teachings above, there is provided an apparatus for driving a 2D transducer array including one or more transducers, in which the apparatus includes a memory 124, and, thus, may reduce a loading time of a large amount of delay time control information and a time taken for a volume scan of a subject and may increase a number of volumes obtainable per second, e.g., a volume rate.

According to teachings above, there is provided an apparatus for driving a 2D transducer array including one or more transducers, in which delay time control information and receiver transducer control information stored in a memory are loaded in parallel in every column, which may serve to reduce a loading time of the memory.

According to teachings above, there is provided an apparatus for driving a 2D transducer array including one or more transducers, in which an enormous amount of data is generated by a front end processing apparatus, transmitted to a memory, and thereby transmitted to the 2D transducer array through one or more drivers, which may serve to reduce a data loading time, maximize a number of scan beam per unit of time, and increase a number of volumes obtainable per second, i.e., a volume rate.

According to teachings above, there is provided an apparatus for driving a 2D transducer array including one or more transducers, in which a multi-channel may be easily extended, driving may be easily controlled when extending the multi-channel, and a data loading time of a driving apparatus may be reduced, thereby serving to increase the number of volumes obtainable per second.

The units described herein may be implemented using hardware components and software components, such as, for example, microphones, amplifiers, band-pass filters, audio to digital convertors, processing devices, and the like. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors. As used herein, a processing device configured to implement a function A includes a processor programmed to run specific software. In addition, a processing device configured to implement a function A, a function B, and a function C may include configurations, such as, for example, a processor configured to implement both functions A, B, and C, a first processor configured to implement function A, and a second processor configured to implement functions B and C, a first processor to implement function A, a second processor configured to implement function B, and a third processor configured to implement function C, a first processor configured to implement function A, and a second processor configured to implement functions B and C, a first processor configured to implement functions A, B, C, and a second processor configured to implement functions A, B, and C, and so on.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. In particular, the software and data may be stored by one or more computer readable recording mediums. The computer readable recording medium may include any data storage device that can store data which can be thereafter read by a computer system or processing device. Examples of the computer readable recording medium include read-only memory (ROM), random-access memory (RAM), CD-ROMs, magnetic tapes, floppy disks, optical data storage devices. In addition, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable storage mediums. In addition, the described unit to perform an operation or a method may be hardware, software, or some combination of hardware and software. For example, the unit may be a software package running on a computer or the computer on which that software is running.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for driving a two-dimensional (2D) transducer array comprising a plurality of transducers, the apparatus comprising:

a 2D array of drivers configured to respectively drive the plurality of transducers, each of the drivers separately comprising a register, a comparator, a pulse frequency setter, a multi-pulse controller, a transmission signal generator, a signal transceiver, a transmission and reception switch, and a reception signal amplifier, all of which are individually included within a respective driver; and a driving controller configured to control the 2D array of drivers, and comprising a memory configured to store delay time control information to control a delay time for transmission beamforming for each of the transducers, and receiver transducer control information to select a receiver transducer from the transducers.

2. The apparatus of claim 1, wherein the memory is further configured to store, after the drivers transmit transmission signals to the transducers, delay time control information for following transmission beamforming and receiver transducer control information for selecting a following receiver transducer.

3. The apparatus of claim 2, wherein the drivers are further configured to perform processing operations with respect to reception signals that correspond to the transmitted transmission signals when the delay time control information for the following transmission beamforming and the receiver transducer control information for selecting the following receiver transducer are being stored in the memory.

4. The apparatus of claim 1, wherein the stored delay time control information and the stored receiver transducer control information are outputted in parallel in every column constituting the 2D array of drivers or row constituting the 2D array of drivers.

5. The apparatus of claim 1, wherein the register is configured to store delay time control information and receiver transducer control information, the delay time control information being configured to control a delay time for transmission beamforming for a respective transducer, the receiver transducer control information being configured to select a receiver transducer from the transducers.

6. The apparatus of claim 5, wherein the transmission and reception switch is turned on or off with reference to the receiver transducer control information.

7. The apparatus of claim 1, wherein the register is configured to output delay time control information, wherein the comparator is configured to compare the outputted delay time control information with a reference code outputted from the driving controller, wherein the pulse frequency setter is configured to set a pulse frequency for transmission beamforming if the outputted delay time control information is equal to the outputted reference code, and wherein the multi-pulse controller is configured to control a number of pulses for the transmission beamforming if the outputted delay time control information is equal to the outputted reference code.

8. The apparatus of claim 1, wherein the transducers correspond to a capacitive Micromachined Ultrasonic Transducer (cMUT), and wherein the drivers correspond to application specific integrated circuits (ASIC).

9. The apparatus of claim 1, wherein the register stores individual beamforming information for a respective driver, and the comparator compares the individual beamforming information to general reference information sent by the driving controller to each of the drivers, to determine whether the respective driver should initiate beamforming for a respective transducer.

10. The apparatus of claim 1, wherein the drivers are configured to drive the transducers on a one-to-one-basis such that the drivers, positioned in the 2D array of drivers, drive a corresponding transducer on the 2D transducer array.

11. The apparatus of claim 1, wherein the drivers are configured to be independently driven.

12. An apparatus for driving a two-dimensional (2D) transducer array comprising a plurality of transducers, the apparatus comprising:

a 2D array of drivers configured to respectively drive the plurality of transducers, each of the drivers separately comprising a register, a comparator, a pulse frequency setter, a multi-pulse controller, a transmission signal generator, a signal transceiver, a transmission and reception switch, and a reception signal amplifier, all of which are individually included within a respective driver; and a memory configured to store delay time control information to control a delay time for transmission beamforming for each of the transducers, and receiver transducer control information to select a receiver transducer from among the transducers, wherein the memory is further configured to store, after the drivers transmit transmission signals to the transducers, delay time control information to control a delay time for following transmission beamforming for each of the transducers, and receiver transducer control information to select a following receiver transducer from the transducers.

13. The apparatus of claim 12, wherein the stored delay time control information configured to control the delay time for transmission beamforming for each of the transducers and the stored receiver transducer control information configured to select the receiver transducer from among the transducers are outputted in parallel in every column constituting the 2D array of drivers or row constituting the 2D array of drivers.

14. The apparatus of claim 12, wherein the register is further configured to output the receiver transducer control information configured to select the receiver transducer from among the transducers, and wherein the transmission and reception switch is turned on or off according to the outputted receiver transducer control information.

15. A medical imaging system, comprising:

a probe comprising a driving apparatus and a front end processing apparatus, the driving apparatus being configured to drive a two-dimensional (2D) transducer array comprising a plurality of transducers, the front end processing apparatus being configured to process reception signals outputted from the driving apparatus, the driving apparatus comprising a 2D array of drivers configured to respectively drive the plurality of transducers, each of the drivers separately comprising a register, a comparator, a pulse frequency setter, a multi-pulse controller, a transmission signal generator, a signal transceiver, a transmission and reception switch, and a reception signal amplifier, all of which are individually included within a respective, wherein the driving apparatus further comprises a memory configured to store delay time control information to control a delay time for transmission beamforming for each of the transducers, and receiver transducer control information to select a receiver transducer from the transducers; and a main system configured to synthesize the reception signals outputted from the probe.

16. The medical imaging system of claim 15, wherein the memory is further configured to store, after the drivers transmit transmission signals to the transducers, delay time control information configured to control a delay time for following transmission beamforming for each of the transducers and receiver transducer control information configured to select a following receiver transducer from the transducers.

* * * * *